(12) United States Patent
Nachum

(10) Patent No.: US 8,112,156 B2
(45) Date of Patent: *Feb. 7, 2012

(54) METHOD AND DEVICE FOR IMPROVING BLOOD FLOW BY A SERIES OF ELECTRICALLY-INDUCED MUSCULAR CONTRACTIONS

(75) Inventor: Zvi Nachum, Tiberias (IL)

(73) Assignee: Lifewave Ltd, Tel-Aviv (IL)

( * ) Notice: Subject to any disclaimer, the term of this patent is extended or adjusted under 35 U.S.C. 154(b) by 651 days.

This patent is subject to a terminal disclaimer.

(21) Appl. No.: 12/168,243

(22) Filed: Jul. 7, 2008

(65) Prior Publication Data

US 2009/0012584 A1 Jan. 8, 2009

Related U.S. Application Data

(62) Division of application No. 10/451,334, filed as application No. PCT/IL02/00035 on Jan. 16, 2002.

(30) Foreign Application Priority Data

Jan. 17, 2001 (IL) .......................................... 140950

(51) Int. Cl.
*A61N 1/00* (2006.01)

(52) U.S. Cl. ................ 607/50; 607/72; 607/74

(58) Field of Classification Search ................ 607/50, 607/74, 46, 48, 72
See application file for complete search history.

(56) References Cited

U.S. PATENT DOCUMENTS

| 5,158,081 A * | 10/1992 | McWhorter et al. ............ 607/50 |
| 5,674,262 A * | 10/1997 | Tumey ............................ 607/48 |
| 2004/0054384 A1 | 3/2004 | Nachum |
| 2009/0012582 A1 * | 1/2009 | Nachum ......................... 607/74 |
| 2009/0012583 A1 * | 1/2009 | Nachum ......................... 607/74 |

\* cited by examiner

*Primary Examiner* — Niketa Patel
*Assistant Examiner* — Alyssa M Alter
(74) *Attorney, Agent, or Firm* — Mark M Friedman

(57) ABSTRACT

A treatment method and device for promoting a localized increase in the flow of blood through a blood vessel in an area of the body, the method including the steps of: (a) providing a system including: (i) at least a first electrode operatively contacting a first portion of body tissue; (ii) at least a second electrode operatively contacting a second portion of body tissue; and (iii) a signal generator, operatively connected to the first electrode and the second electrode, for providing a plurality of electrical impulses to the electrodes; (b) applying the electrical impulses so as to subject the muscular tissue to at least one voltage differential, thereby inducing repeated, contracting, directional movement of muscular tissue associated within the blood vessel, so as to produce a localized increase in the flow of blood through the blood vessel.

4 Claims, 9 Drawing Sheets

(PRIOR ART)

FIG. 10A
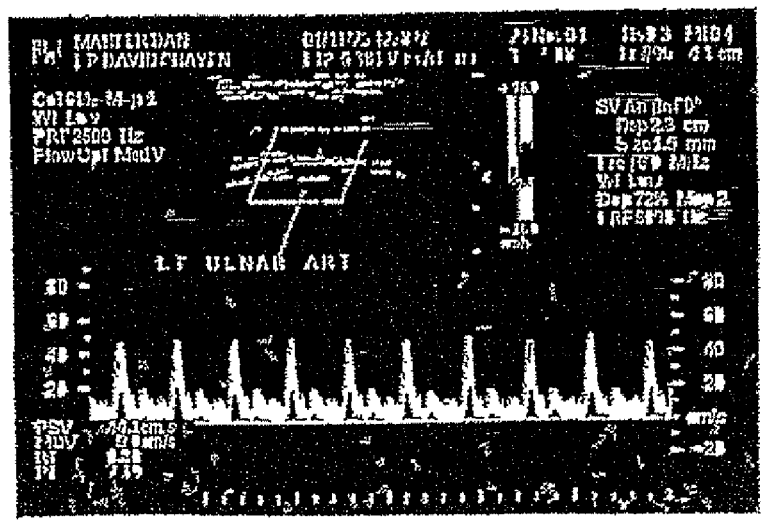
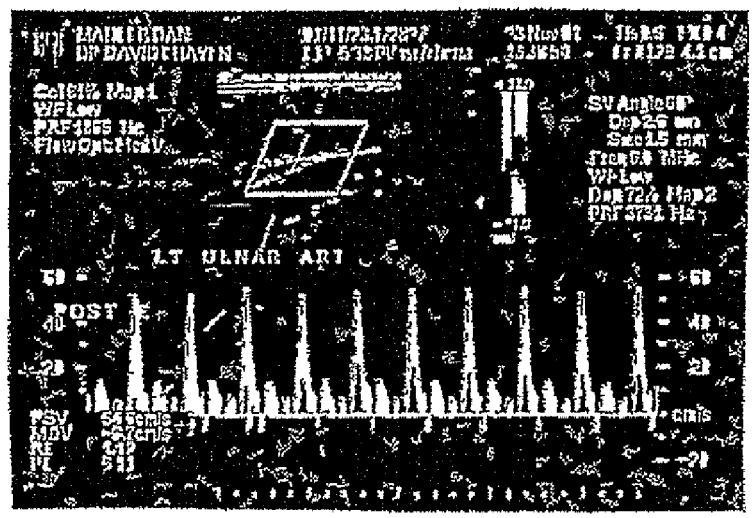
FIG. 10B

METHOD AND DEVICE FOR IMPROVING BLOOD FLOW BY A SERIES OF ELECTRICALLY-INDUCED MUSCULAR CONTRACTIONS

This application claims priority from U.S. patent application Ser. No. 10/451,334 filed 20 Jun. 2003, which claims priority from PCT/IL02/00035, filed 16 Jan. 2002, which in turn claims priority from Israeli Patent Application No. 140950, filed 17 Jan. 2001.

FIELD AND BACKGROUND OF THE INVENTION

The present invention relates to a method of enhancing blood flow, and more particularly, to a method of promoting a localized increase in the flow of blood through a blood vessel by inducement of a repeated, contracting movement of muscular tissue associated with the blood vessel, the inducement being achieved by subjecting the muscular tissue to an electric current. This repeated, contracting movement of muscular tissue creates a peristaltic motion of the blood vessels, thereby increasing the flow of blood. Alternatively, the repeated, contracting movement of muscular tissue can be induced against the flow of blood, such that the flow of blood to a given area is reduced.

The method presented herein is germane to a wide variety of medical applications, including various problems associated with poor blood circulation, improved drainage of retained water, relief of muscle and tissue pain, and therapy related to controlling the functioning of erectile tissue. The stimulation of blood flow is of particular importance for the treatment of sores on extremities and/or in organs suffering from poor blood circulation, e.g., increasing the flow of blood to the toes of a diabetic patient, or increasing the rate at which an edema is drained from a body cavity. The restriction of blood flow is also germane to a wide variety of medical applications, including various surgical procedures.

Current treatments for improving blood circulation and alleviating neural and muscle pain include manual, electrical, and mechanical methods. Manual treatment practiced in physiotherapy requires massage administered by qualified personnel. This art varies according to the experience and technique of each individual massage therapist, and therefore can not be prescribed in an adequately standardized form. The improvement in blood circulation is also of an extremely limited magnitude.

Electrical Muscle Stimulation (EMS) has seen widespread use in many applications. The Food and Drug Administration (Section 355.200 Electrical Muscle Stimulators, CPG 7124.26) maintains that EMS devices are recognized in the health care community as being effective for muscle reeducation, relief of muscle spasm, increasing range of motion, disuse atrophy therapy, increasing local blood circulation, and immediate post-surgical stimulation of calf muscles to prevent venous thrombosis. It must be emphasized, however, that the stimulation provided by EMS is very similar to the stimulation achieved by therapeutic massage. The increase in blood circulation is so modest that it is often undetectable using conventional flow-measuring equipment such as Doppler-based equipment. EMS is a random excitation of a local tissue area. Hence, EMS methods, like therapeutic massage, hot-water treatments, etc. are incapable of providing a major increase in the localized flow of blood. Moreover, because the excitation is random, EMS methods are fundamentally incapable of providing a decrease in the localized flow of blood.

Also known is a sequential pneumatic device for the reduction of an edema. The device consists of several overlapping compartments contained in a sleeve assembly. The compartments are inflated in a sequential fashion, from a distal end disposed adjacent to the edema, to a proximal end, such that the edema is pressed in the proximal direction. Each compartment is filled with air by a pump. The cycle starts with the filling of the distal compartment, and subsequently the remaining compartments are filled until all compartments are full. After a deflation period, the cycle is repeated.

In such electromechanical installations, electric motors, reciprocating mechanisms and the like create uncomfortable noise and vibration. These treatments are of further disadvantage in that they require various device elements to be contacted with the skin. These elements are often a source of discomfort to the patient, and require changing and cleaning after each use in order to ensure good sanitary conditions.

There is therefore a recognized need for, and it would be highly advantageous to have, a method for promoting, regulating, and/or decreasing the localized fluid circulation through blood vessels, according to demand. It would be of further advantage if such a method would be simple, user-friendly, non-invasive, repeatable, and adjustable to the individual needs of the patient.

SUMMARY OF THE INVENTION

According to the teachings of the present invention there is provided a treatment method for promoting a localized increase in a flow of blood through a blood vessel in an area of a body, including the steps of: (a) providing a system including: (i) at least a first electrode operatively contacting a first portion of body tissue; (ii) at least a second electrode operatively contacting a second portion of body tissue, and (iii) a signal generator, operatively connected to the first electrode and the second electrode, for providing a plurality of electrical impulses to the electrodes; (b) applying the electrical impulses so as to subject the muscular tissue to at least one voltage differential, thereby inducing a repeated, contracting, directional movement of muscular tissue associated with the blood vessel, so as, to produce a localized increase in the flow of blood through the blood vessel.

According to another aspect of the present invention there is provided a treatment method for promoting a localized change in a flow of blood through a blood vessel in an area of a body, including the steps of: (a) providing a system including: (i) at least a first electrode operatively contacting a first portion of body tissue; (ii) at least a second electrode operatively contacting a second portion of body tissue, and (iii) a signal generator, operatively connected to the first electrode and the second electrode, for providing a plurality of electrical impulses to the electrodes, and (b) placing the at least a first electrode at one end of the area, and placing the at least a second electrode at a second end of the area, and (c) applying the electrical impulses so as to establish a voltage differential between the electrodes, the voltage differential being made up of two wave forms propagated in opposite directions between the electrodes, so as to produce a localized change in the flow of blood through the blood vessel.

According to another aspect of the present invention there is provided a treatment method for promoting a localized decrease in a flow of blood through a blood vessel in an area of a body, including the steps of: (a) providing a system including: (i) at least a first electrode operatively contacting a first portion of body tissue; (ii) at least a second electrode operatively contacting a second portion of body tissue, and (iii) a signal generator, operatively connected to the first electrode and the second electrode, for providing a plurality of electrical impulses to the electrodes, and (b) applying the electrical impulses so as to subject the muscular tissue to at least one voltage differential, thereby inducing a repeated, contracting movement of muscular tissue associated with the blood vessel, so as to produce a localized decrease in the flow of blood through the blood vessel.

According to yet another aspect of the present invention there is provided a device for promoting a localized change in a flow of blood through a blood vessel, the device including: (a) at least a first electrode operatively contacting a first portion of body tissue; (b) at least a second electrode operatively contacting a second portion of body tissue, and (c) a signal generator, operatively connected to the first electrode and the second electrode, for providing a plurality of electrical impulses to the electrodes, and (d) control means for controlling signals produced by the signal generator, wherein the control means and the signal generator are designed and configured, and the electrodes are displaced, so as to establish a voltage differential between the electrodes, the voltage differential being made up of wave forms propagated in opposite directions between the electrodes, the voltage differential for promoting a localized change in the flow of blood through the blood vessel.

According to features in the described preferred embodiments, the electrical impulses act upon the muscular tissue to produce a periodic, repetitive, undulating motion that imposes on the blood vessel a repetitive periodic motion of peristaltic character.

According to still further features in the described preferred embodiments, the first electrode is a first plurality of electrodes, the second electrode is a second plurality of electrodes, and the providing of the localized increase in the flow of blood is achieved by spacing the electrodes of the first plurality and of the second plurality along a length of the area and establishing sequential and repetitive voltage differences between the electrodes of the first plurality and the electrodes of the second plurality.

According to still further features in the described preferred embodiments, the method further includes the step of: (e) placing the first electrode at one end of the area, and placing the second electrode at a second end of the area, and wherein the voltage differential established between the electrodes is made up of two wave forms propagated in opposite directions so as to obtain a resultant signal of defined direction, frequency and strength whereby the repeated contracting movement of muscular tissue is induced.

According to still further features in the described preferred embodiments, the first electrode is a single first electrode, and the second electrode is a single second electrode.

According to still further features in the described preferred embodiments, the method further includes the step of: (c) optimizing the localized increase in the flow of blood.

According to still further features in the described preferred embodiments, the optimizing is based upon sensory controlled adjustment.

According to still further features in the described preferred embodiments, the optimizing is performed based upon instrumentally measured blood flow.

According to still further features in the described preferred embodiments, the method further includes the step of: (c) obtaining a periodic measurement of the flow of blood through the blood vessel, and (d) optimizing the localized increase or decrease in the flow of blood based upon the measurement.

According to still further features in the described preferred embodiments, the method further includes the step of: (c) modulating a parameter of a wave signal established across the first electrode and the second electrode.

According to still farther features in the described preferred embodiments, the parameter of the wave signal includes a frequency of the wave signal.

According to still further features in the described preferred embodiments, the parameter of the wave signal includes a form of the wave signal.

According to still further features in the described preferred embodiments, the parameter of the wave signal includes a voltage of the wave signal.

According to still further features in the described preferred embodiments, the method further includes the step of: (c) modulating a parameter of the repeated contracting movement to achieve defined target characteristics for the flow of blood.

According to still further features in the described preferred embodiments, a pressure sensor is utilized to measure or indicate the blood flow.

According to still further features in the described preferred embodiments, the method further includes the step of: (c) synchronizing the plurality of electrical impulses with pulses of blood corresponding to heartbeats, to obtain the localized increase in the flow of blood.

According to still further features in the described preferred embodiments, the synchronizing is achieved by monitoring blood pressure in the body.

According to still further features in the described preferred embodiments, the signal consists of a positive voltage differential phase and a negative voltage differential phase, wherein the positive phase and the negative phase have a time overlap.

According to still further features in the described preferred embodiments, the time overlap is between 1 microsecond and 500 microseconds.

According to still further features in the described preferred embodiments, the time overlap is between 10 microseconds and 100 microseconds.

According to still further features in the described preferred embodiments, the signal consists of a plurality of positive voltage differential peaks and a plurality of negative voltage differential peaks, wherein each of the peaks has a duration of 30-500 microseconds.

According to still further features in the described preferred embodiments, each of the peaks has a duration of 50-300 microseconds.

According to still further features in the described preferred embodiments, each of the positive peaks has a duration of 150-300 microseconds.

According to still further features in the described preferred embodiments, the signal consists of a plurality of pulses, each of the pulses including a positive voltage differential phase and a negative voltage differential phase, wherein the plurality of pulses has a frequency in the range of 0.5-150 pulses per second (PPS).

According to still further features in the described preferred embodiments, the plurality of pulses has a frequency in the range of 25-150 PPS.

According to still further features in the described preferred embodiments, the localized change is an increase in the flow of blood through the blood vessel.

According to still further features in the described preferred embodiments, the localized change is a decrease in the flow of blood through the blood vessel.

According to still further features in the described preferred embodiments, the voltage differential is a plurality of voltage differentials.

According to still further features in the described preferred embodiments, the voltage differential is controlled by the control means so as to induce a repeated, contracting, directional movement of muscular tissue associated with the blood vessel, thereby achieving the localized increase in the flow of blood through the blood vessel.

According to still further features in the described preferred embodiments, the control means control the wave forms so as to obtain a resultant signal of defined direction, frequency and strength, whereby a repeated, contracting movement of muscular tissue is induced.

According to still further features in the described preferred embodiments, the device further includes: (e) an instrument for measuring blood flow, operatively connected to the control means.

According to still further features in the described preferred embodiments, the control means are further designed to initiate the sequence of electrical impulses based on an input from the instrument.

According to still further features in the described preferred embodiments, the instrument includes a pressure sensor for producing blood pressure data.

According to still further features in the described preferred embodiments, the control means are further designed to synchronize the sequence of electrical impulses with pulses of blood corresponding to heartbeats.

According to still further features in the described preferred embodiments, the signal generator includes at least two signal generators.

According to still further features in the described preferred embodiments, the device further includes: (e) amplifiers, operatively connected in parallel to the signal generator.

The present invention successfully addresses the shortcomings of the existing technologies by providing a painless, external, non-invasive method of enhancing or reducing a localized flow of blood. The present invention is simple, easy to adjust, and is readily adaptable to the needs of a specific patient.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings:

FIG. 10a is a plot showing blood flow through a blood vessel as a function of time, before implementing the treatment method of the present invention, the blood flow being measured using a Doppler instrument having ultrasound capability for mapping the blood vessel;

FIG. 10b is a plot showing blood flow through a blood vessel as a function of time, using the instrument of FIG. 10a, and applying the treatment method of the present invention;

DESCRIPTION OF THE PREFERRED EMBODIMENTS

Figure 1:
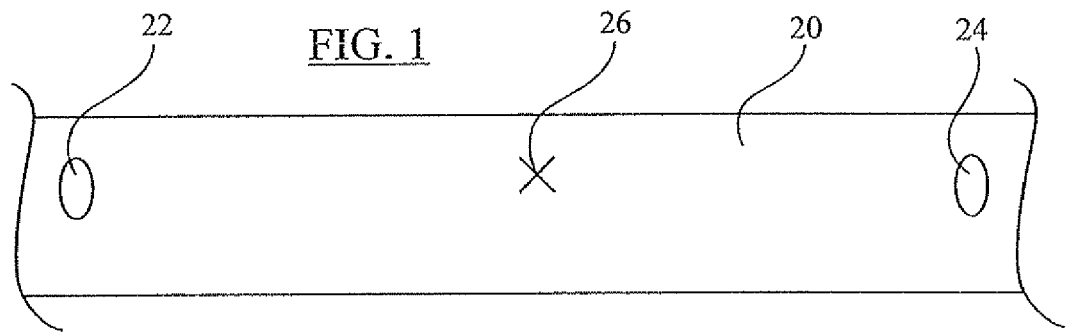
FIG. 1 provides a schematic illustration of a section of a forearm to which are affixed a first electrode and a second electrode, according to the prior art.

According to the teachings of the present invention there is provided a treatment method for promoting a localized increase in a flow of blood through a blood vessel in a particular area of the body.

The principles and operation of this process according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

As used herein in the specification and in the claims section that follows, the term "polarity" refers to any an absolute magnitude of voltage, including zero voltage.

As used herein in the specification and in the claims section that follows, the term "modulated" and "modulation" refer to a process of changing one or more property of electromagnetic energy by methods known in the art and realizable using various commercially available devices.

As used herein in the specification and in the claims section that follows, the term "voltage differential" refers to an absolute difference between two distinct voltage values.

As used herein in the specification and in the claims section that follows, the term "peristaltic" refers to a property common to peristalsis, wherein one or more vessels carrying fluids is compressed in a series of concerted contractions or constrictions in order to move the fluids in a desired direction.

As used herein in the specification and in the claims section that follows, the term "instrumentally measured blood flow" and the like include instrumentally measured flow rates measured using any direct or indirect method. The term is also meant to include any direct or indirect instrumental methods of sensing the heartbeat or the pulsing of blood. Specifically, the term is meant to include methods that utilize pressure sensors to determine relative or absolute blood flow rates, or to sense the pulsing of blood.

In FIG. 1 is provided a schematic illustration of a section 20 of a forearm to which are affixed a first electrode 22 at one end of section 20 and a second electrode 24 at the opposite end of section 20. Electrodes 22, 24 are operatively connected to a power source (not shown). It is known in the art that the application of a suitable voltage differential and current to electrodes 22, 24, results in a contraction of muscular tissue (see FIG. 2). The contraction occurs with a certain time delay, and at a point 26 approximately midway between electrodes 22, 24.

Figure 2:
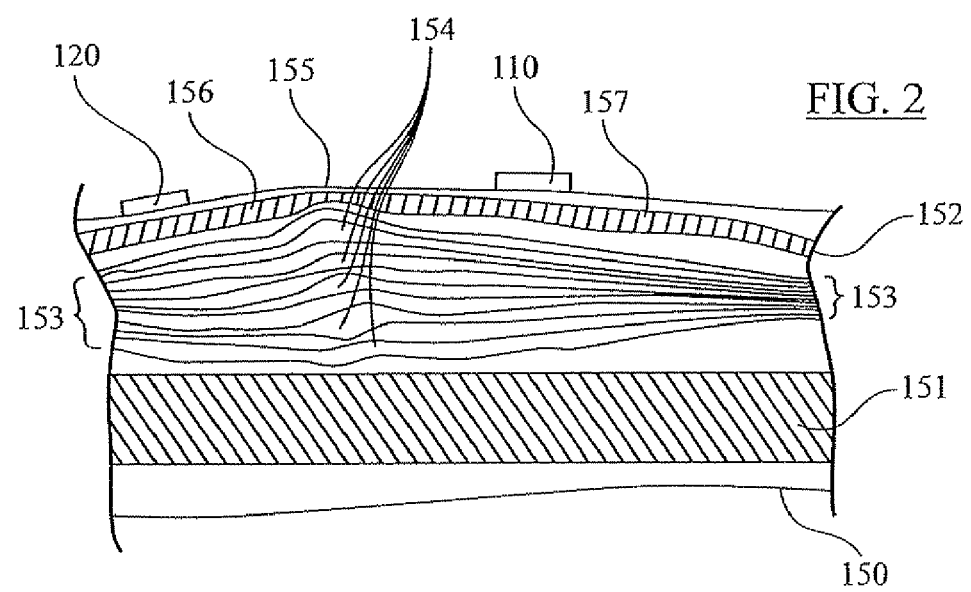
FIG. 2 provides a schematic illustration of the inner tissues of the forearm section of FIG. 1.

In FIG. 2 is provided a schematic illustration of the inner tissues of the forearm section of FIG. 1, which include bone 151, muscle fibers forming muscle 153, and body fluid vessel 152. Vessel 152, (a general term for blood-transporting conduits, which includes, but is not limited to, arteries and veins) located between muscle 153 and skin 150, carries blood substantially along the length of muscle 153.

Subsequent to applying a current to electrode groups 110 and 120, a muscular contractions occurs, causing a bulge or knot 154 in the fibers of muscle 153, thereby impinging upon vessel 152 at constriction point 155.

It has been discovered by the inventor that this phenomenon can be harnessed to enhance the flow of blood through vessel 152. Without wishing to be limited by theory, the inventor attributes the enhanced flow of blood to a peristaltic effect in which the electric current causes such muscular contractions and blood vessel constrictions to occur in series along the length of the muscular tissue. The series of blood vessel constrictions occurs in a very short time frame, such that the flow of blood within the blood vessel is enhanced in a direction predetermined by the form of the electric impulse delivered to the electrodes.

Figure 3:
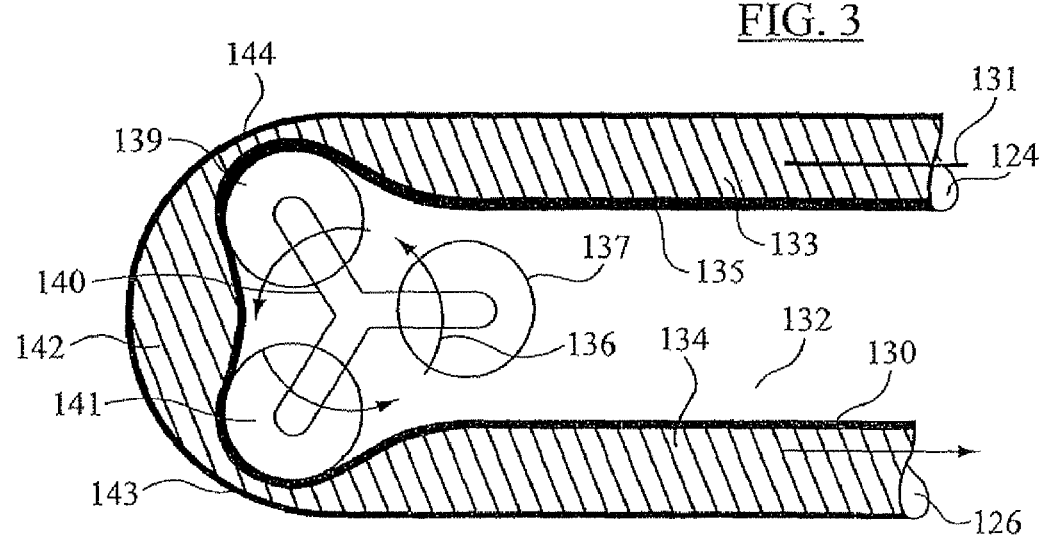
FIG. 3 is a cross sectional diagram depicting the peristaltic pumping principle.

The peristaltic pumping action is better understood by referring to FIG. 3. A typical peristaltic pump utilizes tubing 130 that contains and conveys the pumped fluid. Wall 135 of tubing 130 is typically made of resilient and pliable synthetic material and the tubing 130 is conformed to a U-shaped pattern as shown in the diagram. Against the tubing are disposed-three equidistantly and radially arranged rollers 137, 139 and 141, which are mounted on a frame 140 that is typically driven by any type of electrical motor, in direction 136. The axis of the frame 140 is disposed such that two of the three rollers held thereon cause the tubing 130 to be compressed and constricted: roller 139 creates a constriction point 144 and roller 141 creates a constriction point 143. Subsequent to rotation of the frame 140 in counterclockwise fashion, a pumping action is effected whereby a portion 133 of the fluid is drawn inward in direction 131, a portion 142 of the fluid is entrained between constriction points 143 and 144 created by rollers 141 and 139 respectively, such that portion 142 is caused to move along direction 136, and a portion of fluid 134 is caused to be driven outward in direction 132. Thus, the peristaltic motion causes blood to flow from inlet 124 to outlet 126.

Peristaltic transportation by the wavelike constriction of involuntary muscle tissue is a mechanism used by the body to move food along the length of the alimentary canal. The involuntary muscular walls of arteries can expand or contract to enhance or constrict the flow of blood.

According to the present invention, this principle can be applied by providing a series of external electric impulses, such that the muscular contractions (and hence, the constrictions of an adjacent blood vessel) occur along the length of the muscular tissue in a timely fashion that is conducive to peristaltic flow.

Figure 4:
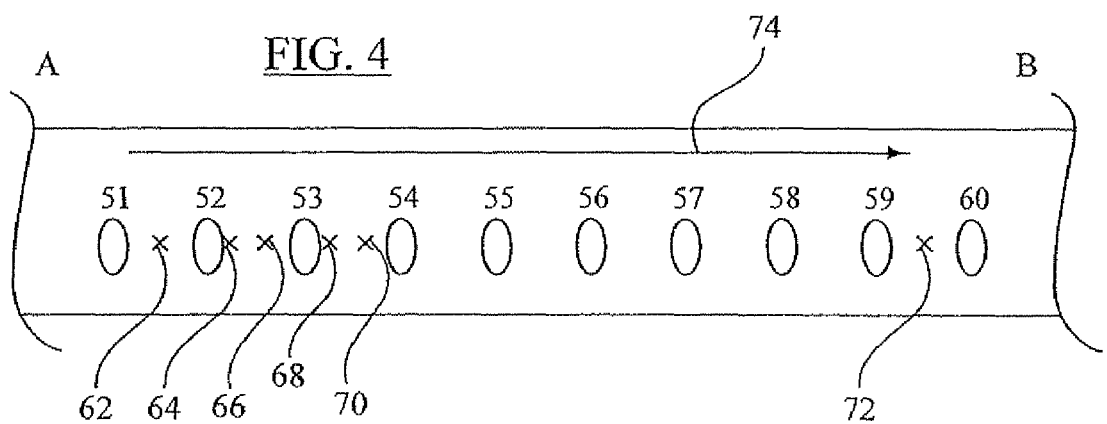
FIG. 4 provides a schematic illustration of a method for enhancing blood flow using a large plurality of electrodes, according to one aspect of the present invention.

The peristaltic pumping effect can be achieved in various ways. FIG. 4, by way of example, provides a schematic illustration of the forearm section 20 shown in FIG. 1, to which are affixed a series of electrodes 51-60 disposed between site A and site B of the forearm section 20. It must be emphasized that in FIG. 4 and in the accompanying description, the number of electrodes, the positioning of the electrodes, and the sequence in which the voltage differential is applied are provided by way of example, in order to illustrate the invention. It will be appreciated by one skilled in the art that many other configurations and sequences are possible.

Electrodes 51-60 are operatively connected to one or more signal generators (not shown), however, for the purpose of this example, a single signal generator is used. The signal generator first provides a suitable voltage differential and current to electrodes 51 and 52, resulting in a contraction of muscular tissue, with a certain time delay, and at a point 62 midway between electrodes 51 and 52. This contraction causes a constriction in a blood vessel adjacent to the muscular tissue, as described above. Subsequently, the signal generator provides a voltage differential to electrodes 51 and 52, resulting in further contraction of muscular tissue, this time at a point 64 approximately midway between electrodes 51 and 53. Subsequently, the signal generator provides a voltage differential to electrodes 51 and 54, resulting in further contraction of muscular tissue, this time at a point 66 midway between electrodes 51 and 54. Subsequently, the signal generator provides a voltage differential to electrodes 51 and 55, resulting in further contraction of muscular tissue, this time at a point 68 midway between electrodes 51 and 55. It may be advantageous to activate an electrode other than electrode 51. Thus, in the next stage of the sequence, the signal generator can provide a voltage differential to electrodes 52 and 55, resulting in further contraction of muscular tissue, this time at a point 70, approximately midway between electrodes 52 and 55. The sequence described above can be continued until the final contraction in the sequence (at point 72) is achieved by supplying a voltage differential to electrodes 59 and 60.

It has thus been demonstrated how a series of muscular contractions can be propagated along a length of muscular tissue, in this case between site A and site B of forearm 20. This series of contractions enhances the flow of blood by constricting an adjacent blood vessel so as to substantially effect peristaltic pumping.

Figure 5:
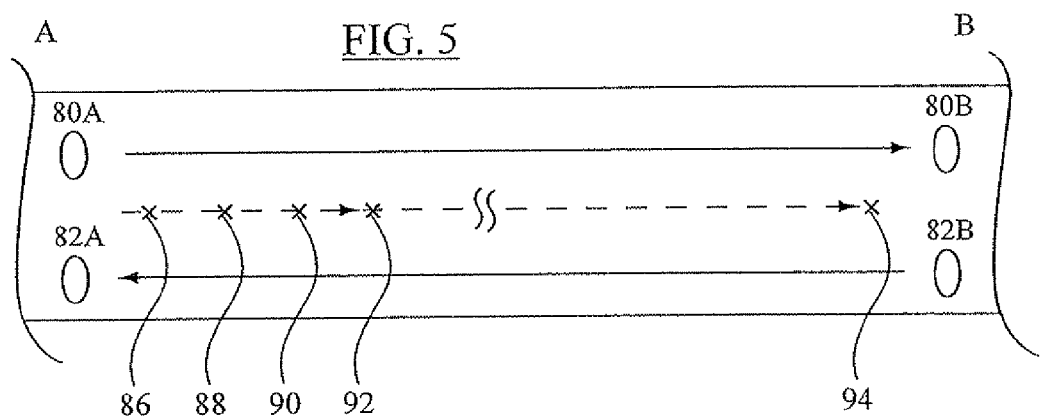
FIG. 5 provides a schematic illustration of a method for enhancing blood flow using two electrode pairs operatively connected to a system having at least two signal generators.
Figure 7A:
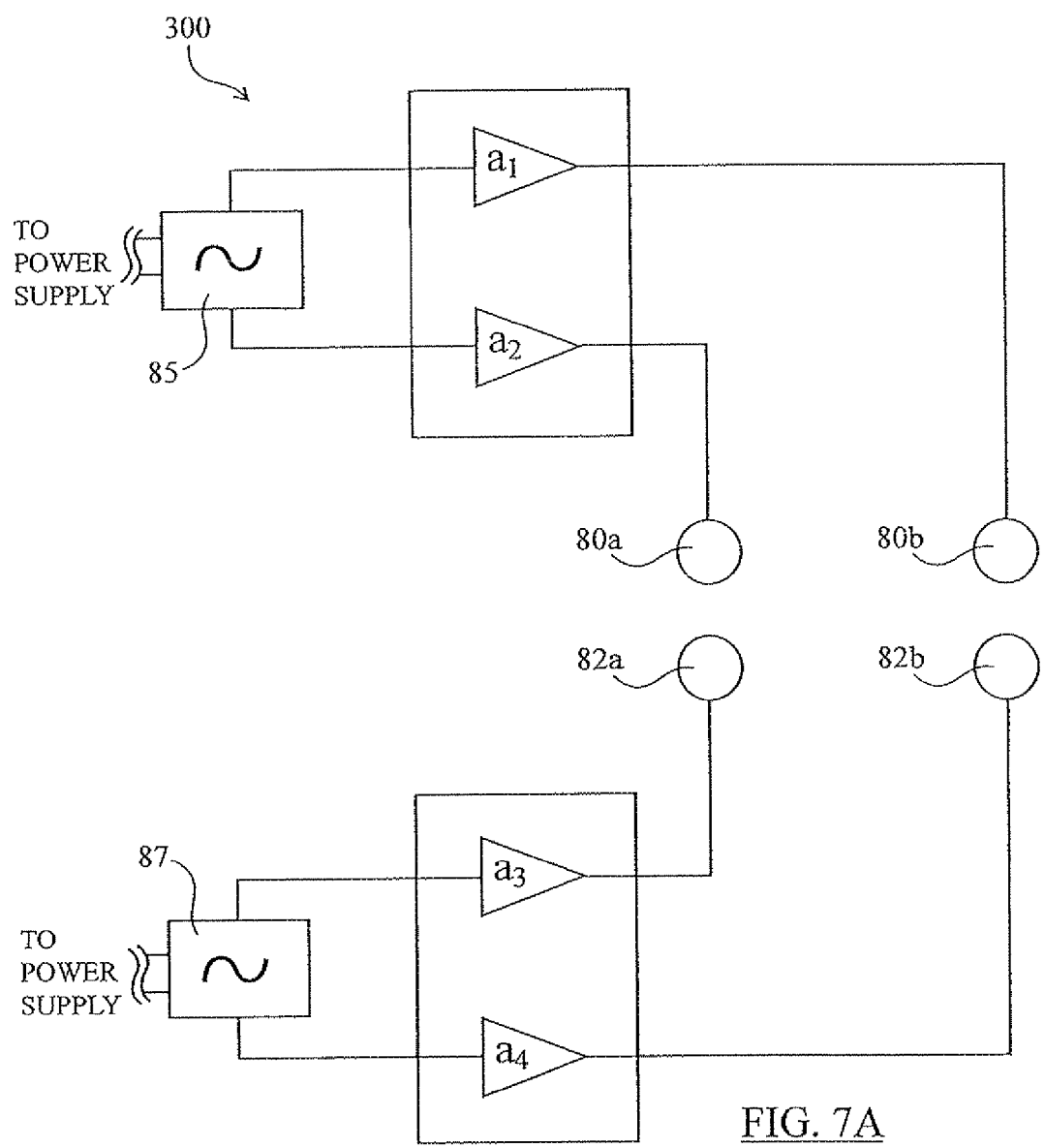
FIG. 7a provides a schematic illustration of a system for enhancing blood flow according to the method described in the description accompanying FIG. 5.

It has been further discovered by the inventor that peristaltic pumping from site A to site B can be effected in such a blood vessel even without the positioning of electrodes across the length between site A and site B, as previously illustrated in FIG. 4. FIG. 5 provides a schematic illustration of the forearm section 20 shown in FIG. 1 and FIG. 4, to which are affixed a first electrode pair, 80A and 80B, and a second electrode pair, 82A and 8211. By way of example, electrodes 80A and 82A are situated near the end of site A, and electrodes 80B and 82B are situated near the end of site B of forearm section 20. As shown in FIG. 7a, each electrode pair is operatively connected to a different signal generator. Initially, a voltage differential is applied to first electrode pair 80A and 80B, by a first signal generator 85. Very shortly thereafter, a voltage differential is applied to second electrode pair 82A and 82B, by a second signal generator 87, wherein the sign on the voltage differential is reversed relative to the initial impulse provided to first electrode pair 80A and 80B.

As a result, the initial muscular contraction does not occur halfway between the above-mentioned electrode pairs, as might be anticipated, but at point 86, close to the end of site A. Without wishing to be limited by theory, it is believed that this phenomenon is related to the fact that a muscle is fundamentally different from an ideal resistor in that a muscle is an extremely complex resistor having an inherent lag time until contraction occurs. In any event, after a short time interval, another voltage differential is applied to first electrode pair 80A and 80B by first signal generator 85. Immediately thereafter, a voltage differential is applied to second electrode pair 82A and 82B, by second signal generator 87, as described above. Consequently, the muscle continues to contract from point 86 to point 88. This sequence is repeated several times, and the point of contraction shifts from point 88 to point 90, from point 90 to point 92, and ultimately, the point of contraction reaches point 94, located near site B. As explained above, the point of constriction of the adjacent blood vessel (see FIG. 3) substantially parallels the point of contraction of the muscular tissue. Thus, the directional constriction of the blood vessel increases the flow within the blood vessel due to the peristaltic effect. If the directional constriction of the blood vessel is opposite to the natural direction of flow in the blood vessel, the peristaltic effect reduces the flow of blood coming from the heart.

Upon reaching point 94, the cycle is reinitiated, with the point of contraction again occurring near point 86.

Figure 8A:
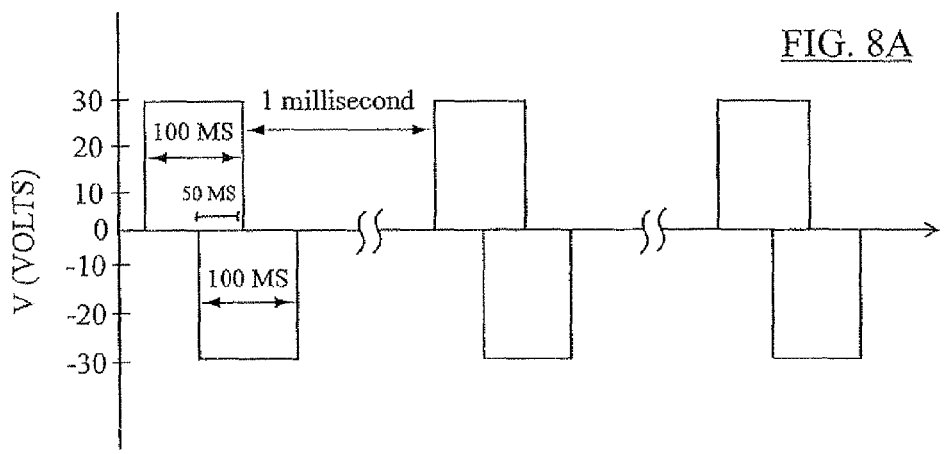
FIG. 8a is a graph showing an exemplary voltage vs. time curve for a treatment method according to the present invention.

Preferably, the voltage differential applied to second electrode pair 82A and 82B by second signal generator 87, wherein the sign on the voltage differential is reversed relative to the initial impulse provided to first electrode pair 80A and SOB, is timed such that the initiation of the voltage differential takes place before the voltage differential applied to first electrode pair 80A and 80B by first signal generator 85 has been terminated. Exemplary voltage vs. time curves are provided in FIGS. 8a and 8b, described in Example 1 below.

Figure 6:
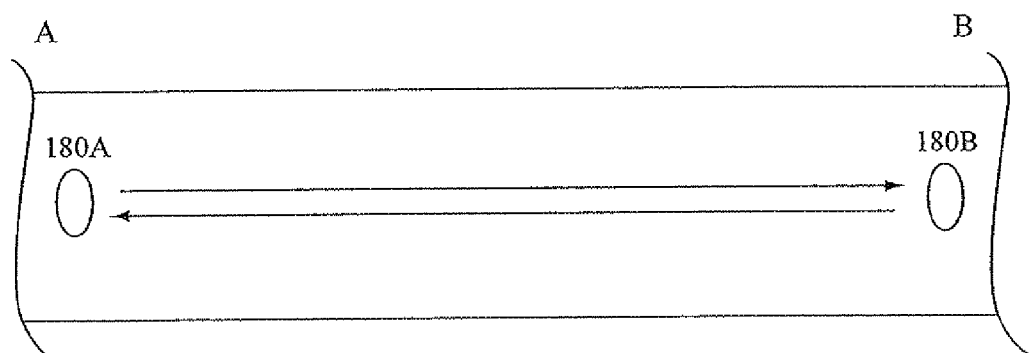
FIG. 6 provides a schematic illustration of a method for enhancing blood flow using a single electrode pair.

FIG. 6 illustrates a more simple configuration of the present invention, one that requires only a single electrode pair. By way of example, FIG. 6 provides a schematic illustration of the forearm section 20 shown in FIGS. 1, 4 and 5, to which is affixed a single electrode pair, 180A and 180B, substantially in the same location as single electrode pair 80A and 80B shown in FIG. 5. Electrode pair 180A and 180B is connected to 4 amplifiers (a1-a4) in a differential floating scheme, as shown in FIG. 7b and as described in further detail below.

This configuration enables each electrode in electrode pair 180A and 180B to change polarity from a positive charge to a negative charge, and vice versa, according to the program that the controller dictates to signal generators 85, 87. In essence, electrode 180A performs the function of electrodes 80A and 82A (FIG. 5), and similarly, electrode 180B performs the function of electrodes 80B and 82B.

FIG. 7a is a schematic electric diagram of the system referred to in the description of FIG. 5. FIG. 7b is a schematic electric diagram of the system referred to in the description of FIG. 6. In FIG. 7a, system 300 includes electrodes 80A and 80B connected to amplifiers a1 and a2, respectively. Amplifiers a1 and a2 are connected to signal generator 85, which is in turn connected to a power supply (not shown). Similarly, electrodes 82A and 82B are connected to amplifiers a3 and a4, respectively. Amplifiers a3 and a4 are connected to signal generator 87, which is in turn connected to a power supply (not shown). When electrodes 80a and 80b (or electrodes 82A and 82B) are electrically contacted to an area of skin on the patient, a current is passed through the area in order to complete the electric circuit.

Figure 7B:
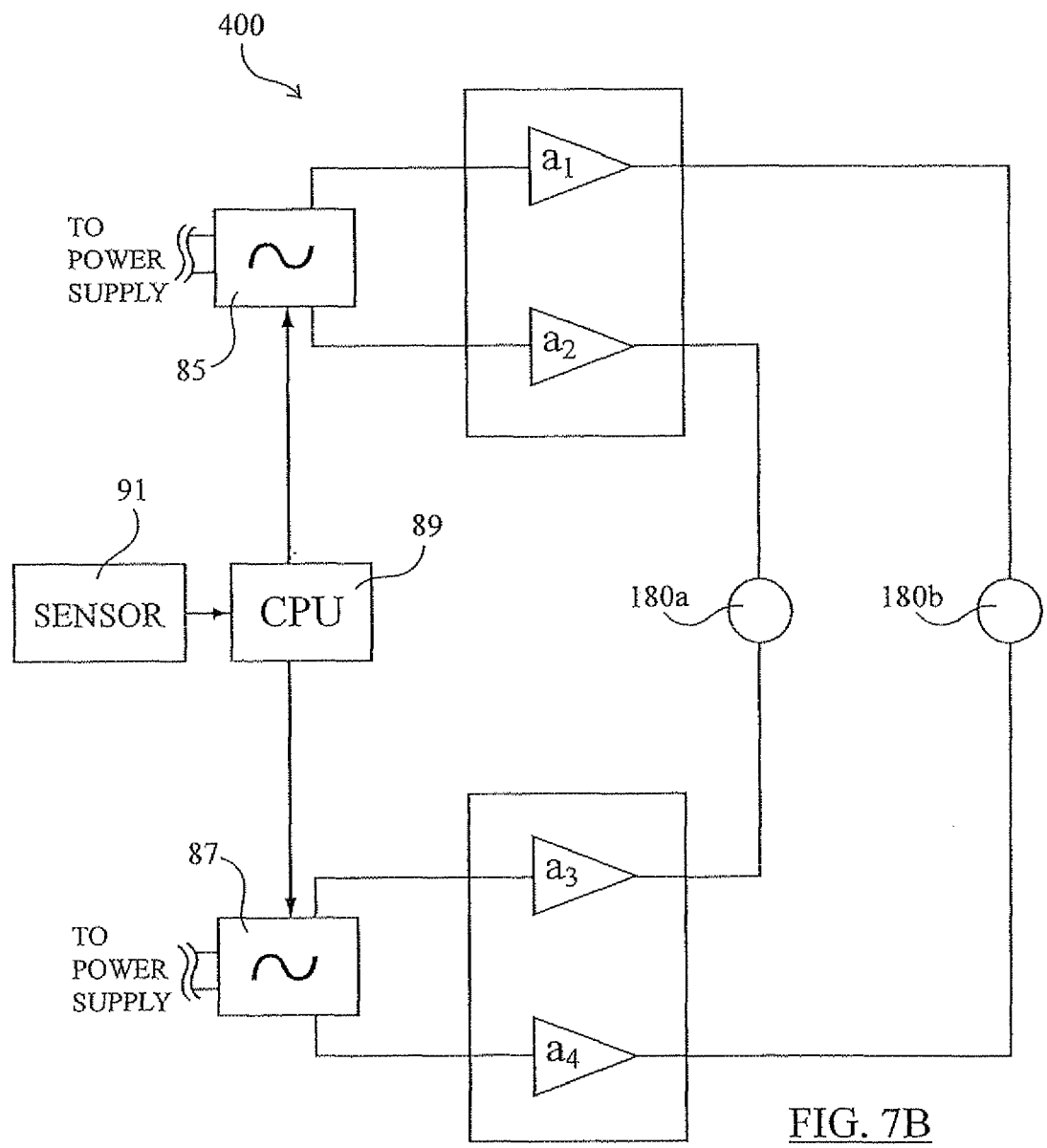
FIG. 7b provides a schematic illustration of a system for enhancing blood flow according to the method described in the description accompanying FIG. 6.

In FIG. 7b, system 400 includes electrode 180A connected to amplifiers a2 and a3, and electrode 180B connected to amplifiers a1 and a4. Amplifiers a1 and a2 are connected to signal generator 85, as in FIG. 7a described above. Similarly, amplifiers a3 and a4 are connected to signal generator 87, as in FIG. 7a. Amplifiers a1-a4 are disposed in a differential floating configuration.

When electrodes 180a and 180b are electrically contacted to an area of skin on the patient, a current is passed through the area in order to complete the electric circuit.

The frequency, the number, the intensity and the duration of muscle contractions are controlled by the modulation characteristics of the current passed to the electrodes. The treatment method of the invention provides for repeating the passing of the modulated voltage to the treated area sufficient number of times so as to affect a localized increase in the flow of blood. This is important in a wide variety of medical applications, including but not limited to rehabilitating muscular response affected by a trauma, inactivity, decreasing the amount of water retained, as in case of the lower limbs, improving blood and lymph circulation, thereby alleviating pain, therapy related to controlling the function of erectile tissue, and speeding up healing, particularly in the case of diabetic patients. The restriction of blood flow by inducing the repeated, contracting movement of muscular tissue against the natural flow of blood is also germane to a wide variety of medical applications, including various surgical procedures.

Various frequencies and wave forms have been found to be effective in the method of the present invention. Appropriate wave forms include square waves, waves of transcendental functions, spikes, linear functions, and stepped patterns. Frequencies vary greatly, depending on the general health of the client, the type and duration of the treatment, etc.

It must also be emphasized that the experienced operator can adjust the wave forms, frequencies, and intensity according to the needs of the individual patient.

In FIG. 7b, the wave form, frequency, etc. produced by signal generator 85 and by signal generator 87 are controlled by CPU 89. In a preferred embodiment of the present invention, the parameters dictated by CPU 89 are pre-determined. It must be emphasized that various frequencies and wave forms have been found to be effective in conjunction with the method of the present invention. Appropriate wave forms include square waves, waves of transcendental functions, spikes, linear functions, and stepped patterns. Frequencies vary greatly, depending on the general health of the client, the type and duration of the treatment, etc. Hence, it is preferable that the device be configured such that an operator can easily adjust such parameters in CPU 89.

Another preferred embodiment, in which the signal generators are controlled by CPU 89 based on input from a sensor 91, is described hereinbelow.

Figure 9A:
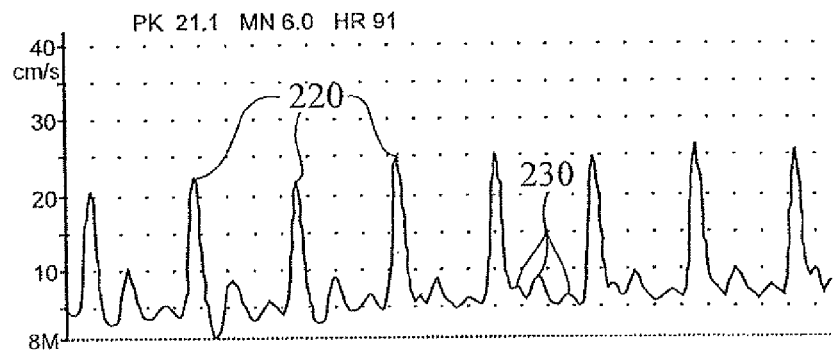
FIG. 9a is a plot showing blood flow through a blood vessel, as a function of time, measured using a Doppler instrument, during a normal period prior to initiating the treatment method of the present invention.

FIG. 9a is a plot showing blood flow through a blood vessel as a function of time, before implementing the treatment method of the present invention. The magnitude of the blood flow is correlated to the linear velocity, which is measured using a Doppler instrument. The major peaks 220 correspond to the linear velocity of the blood through the blood vessel during each pulse (heartbeat). The minor peaks 230 correspond to the linear velocity of the blood through the blood vessel between pulses. The average magnitude of major peaks 220 is 21.1 cm/s; The average magnitude of minor peaks 230 is 6.0 cm/s.

Figure 9B:
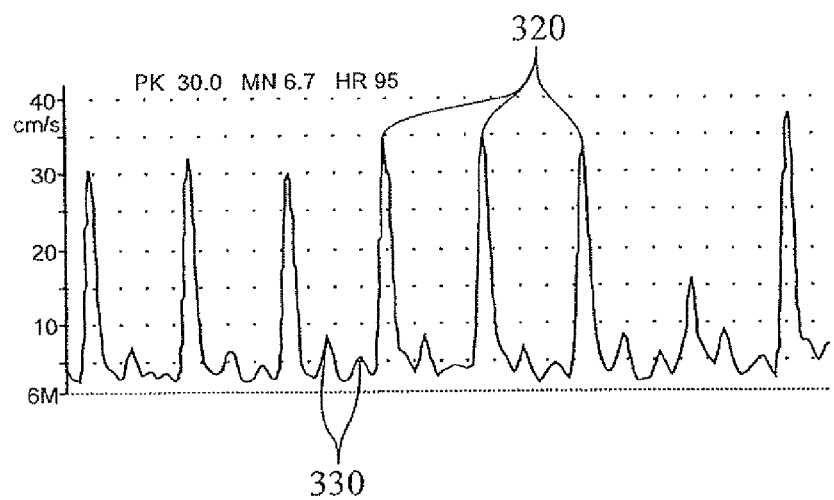
FIG. 9b is a plot showing blood flow through a blood vessel as a function of time, using the treatment method of the present invention.

After completing the plot provided in FIG. 9a, the treatment method of the present invention was implemented on the subject. FIG. 9b shows the linear velocity of the blood flowing through the blood vessel as a function of time. The major peaks 320 have an average magnitude of 30.8 cm/s. The minor peaks 330 have an average magnitude of 6.7 cm/s. Thus, the average magnitude of the major peaks is increased by 40-50%, which indicates an appreciable increase in the local blood flow through the blood vessel.

FIG. 10a is another plot, similar to FIG. 9a, showing the linear velocity of the blood flowing through a blood vessel as a function of time, before implementing the blood flow enhancement (BFE) method of the present invention. The linear velocity is measured using a Doppler instrument having ultrasound capability for mapping the blood vessel.

FIG. 10b is a plot showing the linear velocity of the blood flowing through the blood vessel as a function of time, using the instrument of FIG. 10a, after applying the treatment method of the present invention.

Figure 11A:
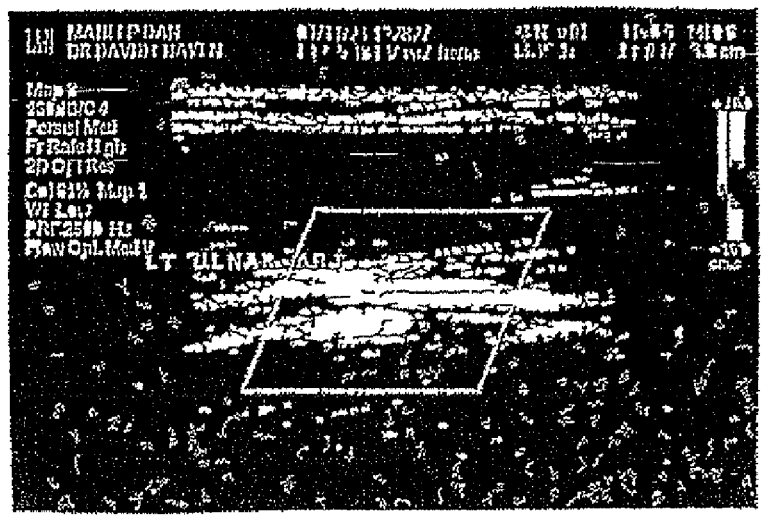
FIG. 11a is a magnified view of the blood vessel mapping shown in FIG. 10a, and FIG. 11b is a magnified view of the blood vessel mapping shown in FIG. 10b.
Figure 11B:
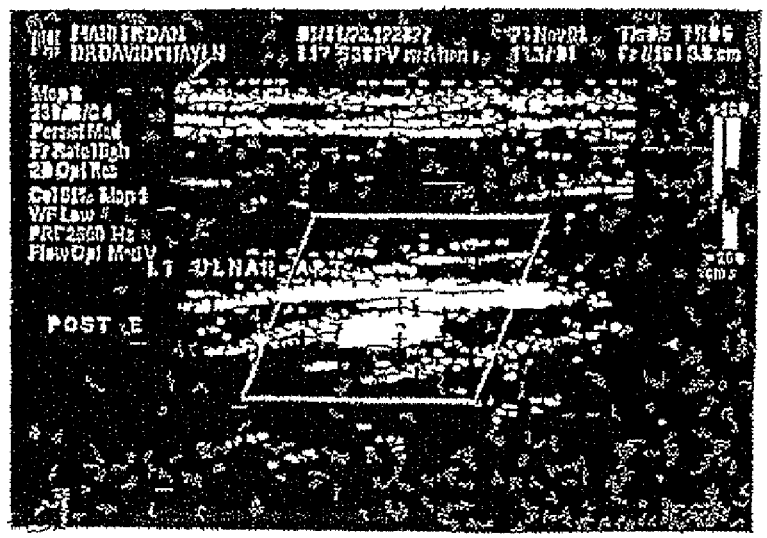

FIG. 11a is a magnified view of the blood vessel mapping shown in FIG. 10a. This view is temporal, as the diameter of the blood vessel is dependent on the volumetric flow rate of the blood, which varies with time and is substantially cyclic with respect to the heartbeat. FIG. 11b is a magnified view of the blood vessel mapping shown in FIG. 10b, in which the inventive BFE method of the present invention is applied. The width of the blood vessel, based on the ultrasound data, was found to have increased relative to the width of the blood vessel in FIG. 11a. The volumetric flow rate through the blood vessel is proportional to the linear velocity multiplied by the cross-sectional area of the blood vessel. The percent increase in linear velocity demonstrated in FIGS. 9a and 9b is multiplied by the square of the width ratio to calculate the percent increase in volumetric flow rate. Hence, the increase in blood flow through the blood vessel is actually even higher than the appreciable increase in blood velocity using the BFE device and method of the present invention.

According to the teachings of the present invention there is provided a treatment method for promoting a localized increase or decrease in a flow of blood through a blood vessel in an area of a body, including the steps of: (a) providing a system including: (i) at least a first electrode operatively contacting a first portion of body tissue; (ii) at least a second electrode operatively contacting a second portion of body tissue, and (iii) a signal generator providing a plurality of electrical impulses having at least one voltage differential to the first electrode and the second electrode, and (b) providing the localized increase or decrease in the flow of blood through the blood vessel by inducement of a repeated, contracting, directional movement of muscular tissue associated with the blood vessel, wherein the inducement is achieved by subjecting the muscular tissue to the voltage differential via the electrodes.

According to further features in the described preferred embodiments, the method further includes optimizing the localized increase or decrease in the flow of blood. The optimizing is preferably based upon sensory controlled adjustment and/or instrumentally measured blood flow.

Although it will be appreciated that one skilled in the art could utilize various and sundry means for instrumentally measuring the blood now or the timing of the heartbeat, as described above, I have found that a pressure sensor is particularly suitable for this function. More specifically, miniature, off-the-shelf pressure sensors such as Motorola Chip Pak High Volume Sensor for Low Pressure Applications (Serial No. MPXC2011DT1) are readily connected to the CPU of the BFE device of the present invention, such that the CPU controls the electric signals produced based on the data obtained from the sensor.

This is more readily understood in conjunction with FIG. 7b, described hereinabove. Sensor 91, which is a pressure sensor, by way of example, is operatively connected to CPU 89 in system 400. Sensor 91 is disposed externally to the skin of the subject, in operative proximity to the rest of system 400. Preferably, sensor 91 is disposed so as to obtain a continuous or semi-continuous reading of the blood pressure in the vicinity of electrode 180a, which is arbitrarily defined to be the electrode that is closer to the heart.

The pressure in blood vessels is characteristically pulsed and substantially cyclic, corresponding to the beating of the heart and the circulation of the blood. Consequently, the maximum flow rate of blood through a blood vessel or a group of blood vessels can be sensed by sensor 91. It has been found that the efficacy of the blood flow enhancement of the present invention is greatly improved when the induced series of muscular contractions is synchronized with the maximum flow rate of blood delivered from the heart. Thus, CPU 89 is preferably configured so as to initiate a new series of muscular contractions (via signal generators 85, 87, amplifiers a1-a4, and electrodes 180a, 180b) upon receiving a maximum reading, close to maximum reading, or a reading above a pre-determined value.

EXAMPLES

Reference is now made to the following examples, which together with the above descriptions, illustrate the invention in a non limiting fashion.

Example 1

FIG. 8 shows an exemplary voltage vs. time graph for a treatment method according to the present invention, using the system described in FIG. 7b and in FIG. 6. The impulses are square waves having an intensity of 30 Volts. The duration of each square wave is approximately 100 microseconds. It should be pointed out that the time axis has not been drawn to scale, in order to fit 3 full cycles in the graph.

The initial impulse provided to electrode pair 180A and 180B by first signal generator 85 voltage has a positive voltage differential (+30 Volts). The second impulse applied to electrode pair 180A and 180B by second signal generator 87, has a reversed charge, i.e., a negative charge of −30 Volts. The second impulse overlaps the first impulse by about 50, such that the second impulse is terminated about 50 microseconds after the first impulse has been terminated.

The time interval between positive impulses (or between negative impulses) is approximately 1 millisecond. Although only 6 impulses are shown in FIG. 8, it will be appreciated that a practical treatment requires a large plurality of such impulses.

Figure 8B:
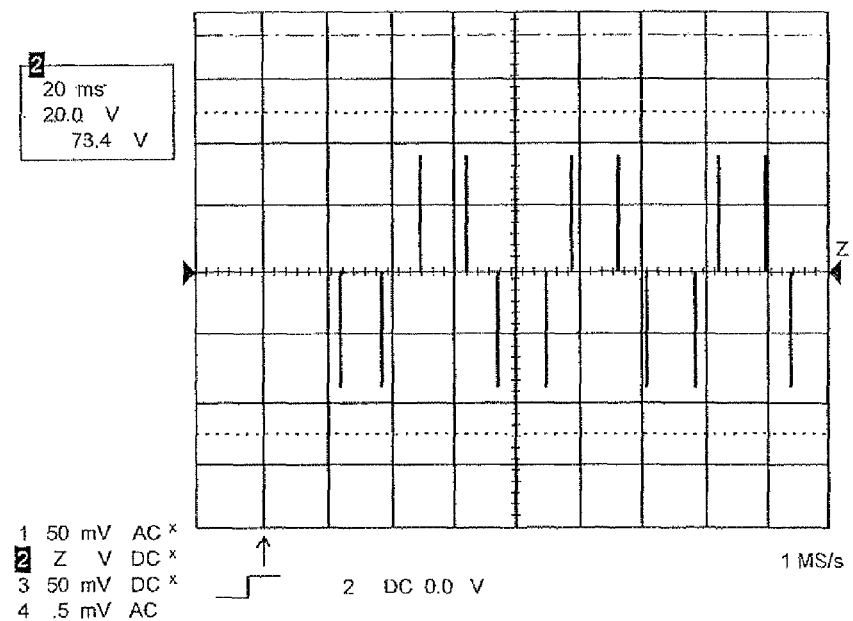
FIG. 8b is a graph showing another exemplary voltage vs. time curve for a treatment method according to the present invention.

FIG. 8b is an oscilloscope tracing showing another exemplary voltage vs. time curve for a treatment method according to the present invention. Each individual pulse (or spike) has a voltage of .about.35V and a duration of 250 microseconds. The sequence is characterized by 2 positive spikes followed by 2 negative spikes. The load is approximately 500 ohms.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A device for promoting a localized change in a flaw of blood through a blood vessel proximate to body tissue, the device comprising:
    (a) a first electrode pair consisting of a first electrode adapted to operatively contact a first portion of body tissue and second electrode adapted to operatively contact a second portion of body tissue;
    (b) a second electrode pair consisting of a third electrode adapted to operatively contact a portion of body tissue in proximity of said first electrode and a fourth electrode adapted to operatively contact portion of body tissue in proximity of said second electrode, and
    (c) a signal generator, operatively connected to said first electrode pair and said second electrode pair, for providing a plurality of electrical impulses to said electrodes, and
    (d) a control mechanism for controlling said plurality of electrical impulses produced by said signal generator, wherein said control mechanism and said signal generator are designed and configured such that when said electrodes are displaced so as to contact, respectively, said first and second portions of said body tissue, a voltage differential established induces a cyclic series of contractions of muscular tissue associated with the blood vessel,
wherein said signal generator varies a time interval between delivery of successive ones of said electrical impulses such that a position of each successive contraction within said series of contractions progresses directionally along a length between said portions of body tissue so as to produce the localized change in the flow of blood through the blood vessel.

2. The device of claim 1, wherein said control mechanism controls said plurality of electrical impulses so as to obtain a resultant signal of defined direction, frequency and strength, whereby said cyclic series of contractions of muscular tissue is induced, said signal including a positive voltage differential phase and a negative voltage differential phase, wherein said positive phase and said negative phase have a time overlap.

3. The device of claim 2, wherein said time overlap is between 1 microsecond and 500 microseconds.

4. The device of claim 1, wherein each of said impulses has a frequency in the range of 0.5-150 pulses per second (PPS).

* * * * *

UNITED STATES PATENT AND TRADEMARK OFFICE
CERTIFICATE OF CORRECTION

| | | |
|---|---|---|
| PATENT NO. | : 8,112,156 B2 | Page 1 of 1 |
| APPLICATION NO. | : 12/168243 | |
| DATED | : February 7, 2012 | |
| INVENTOR(S) | : Zvi Nachum | |

It is certified that error appears in the above-identified patent and that said Letters Patent is hereby corrected as shown below:

ON THE TITLE PAGE:

Item (73) should be corrected as follows:

Change:
--Lifewave Ltd, Tel-Aviv--
to
"Lifewave Ltd, Petach-Tikva"

IN THE CLAIMS:

Column 13, Claim 1 line 18 should be corrected as follows:
Change:
--adapted to operatively contact portion of body tissue in ....--
to
"adapted to operatively contact a portion of body tissue in ...."

Signed and Sealed this
Twenty-seventh Day of March, 2012

David J. Kappos
*Director of the United States Patent and Trademark Office*